(12) United States Patent
Bakhit et al.

(10) Patent No.: US 6,984,628 B2
(45) Date of Patent: Jan. 10, 2006

(54) OPHTHALMIC COMPOSITIONS COMPRISING TREFOIL FACTOR FAMILY PEPTIDES

(75) Inventors: Peter G. Bakhit, Huntington Beach, CA (US); Orest Olejnik, Coto De Caza, CA (US); Richard Graham, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/621,053

(22) Filed: Jul. 15, 2003

(65) Prior Publication Data

US 2005/0014691 A1 Jan. 20, 2005

(51) Int. Cl.
*A61K 38/02* (2006.01)
*A61K 38/17* (2006.01)

(52) U.S. Cl. .......................... 514/21; 514/2
(58) Field of Classification Search ............... 514/2, 514/8, 12, 21
See application file for complete search history.

(56) References Cited

U.S. PATENT DOCUMENTS

| | | | |
|---|---|---|---|
| 4,839,342 A * | 6/1989 | Kaswan | 514/11 |
| 5,474,979 A | 12/1995 | Ding et al. | 514/11 |
| 5,620,921 A | 4/1997 | Sullivan | 514/178 |
| 5,652,209 A | 7/1997 | Pflugfelder et al. | 514/2 |
| 5,688,765 A | 11/1997 | Sullivan | 514/12 |
| 5,900,407 A | 5/1999 | Yerxa et al. | 514/47 |
| 5,958,912 A | 9/1999 | Sullivan | 514/177 |
| 5,981,607 A | 11/1999 | Ding et al. | 514/785 |
| 6,056,950 A * | 5/2000 | Saettone et al. | 424/78.04 |
| 6,063,755 A | 5/2000 | Podolsky | 514/2 |
| 6,107,289 A | 8/2000 | Sullivan | 514/178 |
| 6,153,607 A | 11/2000 | Pflugfelder et al. | 514/178 |
| 6,221,840 B1 | 4/2001 | Podolsky | 514/12 |
| 6,277,855 B1 | 8/2001 | Yerxa | 514/256 |
| 6,316,218 B1 | 11/2001 | Podolsky | 435/69.1 |
| 6,319,908 B1 | 11/2001 | Yerxa et al. | 514/51 |
| 6,323,187 B1 | 11/2001 | Yerxa et al. | 514/51 |
| 6,331,529 B1 | 12/2001 | Yerxa et al. | 514/47 |
| 6,348,508 B1 | 2/2002 | Denick, Jr. et al. | 514/772.4 |
| 6,348,589 B1 | 2/2002 | Pendergast et al. | 536/25.6 |
| 6,432,934 B1 * | 8/2002 | Gilbard | 514/152 |
| 6,436,910 B1 | 8/2002 | Yerxa et al. | 514/47 |
| 6,455,583 B1 | 9/2002 | Pflugfelder et al. | 514/528 |
| 6,525,018 B1 | 2/2003 | Podolsky | 514/2 |
| 6,548,658 B2 | 4/2003 | Yerxa | 536/26.22 |
| 6,555,675 B2 | 4/2003 | Rideout et al. | 536/25.6 |
| 6,585,987 B1 | 7/2003 | Fransoni | 424/401 |
| 2002/0037842 A1 | 3/2002 | Leahy et al. | 514/8 |
| 2002/0119104 A1 | 8/2002 | Rosenthal et al. | 424/49 |
| 2002/0151472 A1 | 10/2002 | Thim et al. | 514/8 |
| 2003/0032585 A1 * | 2/2003 | Thim et al. | 514/8 |
| 2003/0153496 A1 * | 8/2003 | Thim et al. | 514/12 |

FOREIGN PATENT DOCUMENTS

| | | |
|---|---|---|
| EP | 0473159 | 3/1992 |
| EP | 0590655 | 4/1994 |
| WO | WO 02/46226 A2 | 6/2002 |
| WO | WO 02/085402 | 10/2002 |
| WO | WO 02/102399 A2 | 12/2002 |
| WO | WO 02/102403 | 12/2002 |

OTHER PUBLICATIONS

Allen, et al., The mucus barrier, its role in gastroduodenal mucosal protection, *J. Clin Gastroenterol*, 1998; 10 (Suppl1): S93-S98;.

Babyatsky, M.W., et al.,Oral trefoil peptides protect against ethanol-and indomethacin-induced gastric injury in rats, *Gastroenterology*, 1996, vol. 110, pp. 489-497.

Carr, M. D., et al., Solution Structure of Trefoil factor family proteins, *Univ. of Kent* , 3 pgs, www.biochem.ucl.ac.uk, (Feb. 13, 2003).

Corfield, A.P., et al., Ocular mucins: purification, metabolism and functions, *Progress in Retinal and Eye Research*, vol. 16, No. 4, pp 627-656, 1997.

Danjo, Y., et al., Alteration of mucin in human conjunctival epihtelia in dry eye, *Invest Ophthalmol Vis Sci*, 1998, V 39, pp 2602-09.

Dignass, A., et al., Trefoil peptides promote epithelial migration through a transforming growth factor $\beta$-independent pathway, *J. Clin. Invest.* 94, 376-383, (Jul. 1994).

Gipson, I.K., et al., Mucin genes expressed by the ocular surface epithelium, *Progress in Retinal and eye research*, vol. 16, No. 1, pp. 81-98, 1997.

Good, R.J., Surface free energy of solids and liquids: thermodynamics, molecular forces, and structures, *J. Colloid Interface Sci.*; 1977, 59:398-419.

Goke,M., et al., Trefoil peptides promote restitution of wounded corneal epithelial cells, *Experimental Cell Research*, 2001, V. 264, pp. 337-344.

Hauser, F., et al., Hp1.b, A human P-domain peptide homologous with rat intestinal trefoil factor, is expressed also in the ulcer-associated cell lineage and the uterus, *Proc Natl Acad Sci USA*, 1993, V. 90, pp. 6961-6965.

(Continued)

*Primary Examiner*—Jeffrey Edwin Russel
(74) *Attorney, Agent, or Firm*—Brent A. Johnson; Robert J. Baran; Martin A. Voet

(57) ABSTRACT

This invention relates to compositions comprising trefoil family factor peptides which are useful in preventing or treating dry eye by topical administration of the composition to eye of the patient. One aspect of this invention relates to topical ophthalmic compositions comprising a trefoil factor family peptide, and preferably, a mucoadhesive component, as described herein. Another aspect of this invention relates to the use of these compositions to treat or prevent dry eye in a patient.

3 Claims, No Drawings

OTHER PUBLICATIONS

Jagla, W., et al., Localization of TFF3 peptide to porcine conjunctival goblet cells, *Cell tissue res* (1999) 296:525-530.

Langer, G., Secretory peptides TFF1 and TFF3 synthesized in human conjunctival goblet cells, *Invest Ophthalmol Vis Sci*, 1999, V. 40, pp 2220-2224.

Langer, G., Et Al., TFF Peptides, New Mucus-Associated Secretory Products Of The Conjunctiva, *Opthalmologe*, 2001-98:976-979.

Ligumsky, et al., Sucralfate protection against gastrointestinal damage: possible role of prostanoids, *Isr J Med Sci* 1986; 22:801-806.

Paulsen, F.P., et al., TFF peptides in the human efferent tear ducts, *Invest Ophthalmol Vis Sci*, 2002, V 43, pp. 3359-3364.

Playford, R.J., Trefoil peptides: what are they and what do they do?, *Journal of the Royal College of Physicians of London*, vol. 31, pp. 37-40, (Jan./Feb. 1997).

Rachmilewitz, D., Trefoil peptides: a novel modality to prevent gastric injury?, *Gastroenterology*, vol. 110, No. 2, pp. 632-635, (Feb. 1996).

Tabor, et al., Surface Forces and Surface Interactions, *J. Colloid Interface Sci*, 1977, 58:2-13.

Tran, C.P., et al., Trefoil peptide TFF2 (spasmolytic polypeptide) potently accelerates healing and reduces inflammation in a rat model of colitis, *OVID: Tran: Gut*, vol. 44(5) May 1999, 636-642.

Uebermuth, C., Mucins of the eye, *Ophthalmologe*, 1999—96:563-569.

Wong, W.M., et al., Trefoil Peptides, *Gut*, vol. 44(6) Jun. 1999, 890-895.

Williams, et al., Trefoil factor family domain peptides, *Virchows arch*, 1997 431:299-304.

Wright, N.A., Interaction of trefoil family factors with mucins: clues to their mechanism of action?, *Gut*, vol. 48(3) Mar. 2001, pp 293-294.

Teraing and Dry Eyes, *Ocular Times, Eye News and Information*; www.geocities.com/ocular_times/tearing.html, Feb. 14, 2003, 4 pgs.

\* cited by examiner

OPHTHALMIC COMPOSITIONS COMPRISING TREFOIL FACTOR FAMILY PEPTIDES

FIELD OF THE INVENTION

The present invention relates to pharmaceutical compositions. In particular, the present invention relates to topical ophthalmic compositions comprising a trefoil factor family peptide.

BACKGROUND OF THE INVENTION

Description of Related Art

Dry eye disease is a general term for a variety of conditions characterized by abnormalities in the tear film, which affects three million people in the United States alone. Dry eye is characterized by symptoms such as a sandy-gritty feeling in the eye, burning, irritation, or a foreign-body sensation that worsens during the day. Patients suffering from dry eye disease complain of mild to severe symptoms, and those with severe symptoms may experience constant and disabling eye irritation, and develop ocular surface epithelial disease and sight-threatening sterile or microbial corneal ulceration.

The tear film consists of an inner mucous layer, a middle aqueous layer which forms the bulk of the tear film, and an outer lipid layer. The aqueous layer is secreted by the lacrimal gland and the accessory lacrimal glands, and the tear fluid is drained by the efferent tear ducts. While the underlying causes of dry eye diseases are largely unknown, it is generally accepted that they are associated with abnormalities in the tear composition or flow, which are affected by a variety of factors including aqueous layer secretion through lacrimal gland and drainage through the efferent tear passage. In addition to abnormalities in the lacrimal glands, abnormalities in the meibomian glands (which secrete the lipid layer), and abnormalities in drainage through the efferent tear duct passage, changes in mucin composition and mucous viscosity may also affect tear flow [Langer G, et al, *Invest Ophthalmol Vis Sci*, 1999, vol. 40, pp. 2220–2224; Danjo Y, et al, *Invest Ophthalmol Vis Sci*, 1998, vol. 39, pp. 2602–2609; and Paulson F P, et al., *Invest Ophthalmol Vis Sci*, 2002, vol. 43, pp. 3359–3364].

Until recently, the only methods used to treat dry eye disease were topical administration of over-the-counter compositions that serve as artificial tears (such as Refresh® marketed by Allergan, Inc), or surgery to close efferent drainage. Recently, a topical ophthalmic product containing Cyclosporin A, marketed by Allergan Inc., as Restasis®, was introduced, which has shown to be effective in treating many cases of dry eye. However, to maximize the number of options available to the physician and the patient any new and effective treatment for dry eye disease is highly desirable.

Trefoil peptides, or trefoil factor family (TFF) peptides are a class of peptides which comprise a common structural motif, known as the trefoil domain, as part of their structure. The trefoil motif comprises about 20 to about 60 amino acid residues (usually about 40) containing six cysteine residues. The six cysteine residues form three disulfide bridges that complete three loops in the peptide chain so that the roughly 40 residues have a clover-like shape, known as the trefoil domain. TFF-peptides can have one or two trefoil domains per molecule, and may comprise additional amino acid residues which are not part of the trefoil domain. To date, three type of TFF-peptides have been isolated from humans- TFF1 (also known as pS2), TFF2 (also known as SP), and TFF3 (also known as ITF). TFF1 and TFF3 peptides each contain one trefoil domain, while TFF2 peptides contain two trefoil domains. TFF1 and TFF2 peptides are both produced by mucus-producing cells of stomach, while TFF3 peptides are produced by goblet cells of small and large intestine.

All three forms of TFF-peptides are known to be produced in epithelial cells around areas of damage to mucus membrane, suggesting that trefoils have a role in healing injury, particularly to epithelial cells. It is believed that TFF-peptides assist healing by both stabilizing mucus membrane at the injury site and by stimulating repair. It has been shown that TFF-peptides noncovalently link mucin, thus influencing the rheology (e.g. increases viscosity) of mucus gels. [Hauser F, Poulsom R, Chinery R, et al, *Proc Natl Acad Sci USA*, 1993, vol. 90, pp. 6961–6965; and Babyatsky M W, deBeaumont M, Thim L, Podolky D K, *Gastroenterology*, 1996, vol. 110, pp. 489–497]. TFF-peptides also appear to be responsible for promoting the migration of epithelial cells to the site of injury, thus stimulating repair. [Goke M, et al, *Experimental Cell Research*, 2001, vol 264, pp. 337–344; and Playford R J, Journal of the Royal College of Physicians of London, vol 31, pp. 37–40]

Although there is still a great deal unknown about the role of TFF peptides on the ocular surface, in the lacrimal gland, in the efferent passages, and in surrounding tissue, it is believed that TFF-peptides may be present during healing and other related processes in the eye. Biosynthesis and storage TFF1 and TFF3 peptides, but not TFF2, is known to occur in the human conjunctival epithelium [Langer G, et al, *Invest Ophthalmol Vis Sci*, 1999, vol. 40, pp. 2220–2224], and in vitro studies have shown that TFF2 and TFF3 peptides promote the migration of wounded corneal epithelial cells from rabbits [Göke M, et al, *Experimental Cell Research*, 2001, vol 264, pp. 337–344]. However, to the best of our knowledge, no direct relationship has been unambiguously established between TFF-peptides and any pathological condition affecting the eye.

As mentioned previously, some cases of dry eye may be related to mucin composition and the Theological properties of the corresponding mucous membrane. Some work has also suggested that TTF-peptide secretion might be influenced by alterations in mucins as they occur in patients with dry eye symptoms [Danjo and Paulson]. However, to the best of our knowledge, there is no direct evidence in any prior art demonstrating that TFF-peptide secretion abnormalities contribute to the symptoms or cause of dry eye disease. In making the above statements, the applicants make no admission as to whether any of the references cited herein are prior art.

SUMMARY OF THE INVENTION

Surprisingly, compositions comprising trefoil family factor peptides will be useful in preventing or treating dry eye by topical administration of the composition to eye of the patient. One aspect of this invention relates to a topical ophthalmic composition comprising a therapeutically effective amount of a trefoil factor family (TFF) peptide. Another aspect of this invention relates a method of preventing or treating dry eye in a person comprising topically administering to the eye of said person a composition comprising a therapeutically effective amount of a trefoil factor family peptide. Another aspect of this invention relates to a pharmaceutical product comprising a composition having a therapeutically effective concentration of a trefoil factor family peptide which is dispensed from a package suitable for ophthalmic use, wherein the use of the composition for the prevention or treatment of dry eye is indicated thereon.

DETAILED DESCRIPTION OF THE INVENTION

The term trefoil factor family (TFF) peptide as used herein refers to any peptide, whether natural or synthetic, which comprises the trefoil motif described previously herein. That is, the TFF-peptide comprises a residue comprising from 20 to about 60 amino acids, including six cysteine residues. The cysteine residues form disulfide bonds which cause the peptide residue to have a clover-like shape comprising three loops. The methods of preparing of TFF-peptides, such as recombinant expression of peptides and synthetic peptide synthesis, are well known in the art. For example, methods of preparing TFF-peptides are included in the following references: U.S. Pat. No. 6,525,018; Allen, et. al., *J Clin Gastroenterol* 1998; 10 (Suppl 1): S93–S98; Ligumsky, et. al., *Isr J Med Sci* 1986; 22:801–806; Dignass, et. al., *J. Clin. Invest.*, 94, 376–383; Babyatsky, et. al., *Gastroenterology*, 110, 489–497; Hauser, et. al., *Proc. Natl. Acad. Sci. USA*, vol. 90, pp. 6961–6965, August 1993; WO 02102403; and WO02085402, incorporated herein by reference. A therapeutically effective amount of a TFF-peptide can be determined by a person of ordinary skill in the art without undue experimentation. Although any TFF-peptide can be used in any of the compositions described herein related to this invention, it is preferable that TFF1 or TFF3 be used, and more preferred that TFF1 be used. In compositions of this invention the concentration of the TFF-peptide is preferably from about 0.001% to about 1%. More preferred is a concentration of about 0.01% to about 0.5%, and even more preferred is a concentration of about 0.1% to about 0.2%. In the most preferred embodiment of the invention, the concentration of the TFF-peptide is about 0.15%.

In relation to any of the compositions described herein related to this invention, it is preferable the composition also comprise a mucoadhesive component. With respect to this invention, the term "mucoadhesive" means a natural or synthetic component, including macromolecules, polymers, and oligomers, or mixtures thereof, that can adhere to a subject's mucous membrane. Adhesion of mucoadhesives to the mucous membrane occurs primarily through noncovalent interactions, such as hydrogen bonding and Van der Waal forces (Tabor et al., 1977 J. Colloid Interface Sci. 58:2 and Good 1977 J. Colloid Interface Sci. 59:398). While not intending to be bound in any way by theory, it is believed that mucoadhesives will be synergistic with TFF-peptides because they provide targeted delivery of the peptides to the mucous membrane by virtue of their adhesion. This synergy will be particularly pronounced in the case of topical ophthalmic administration of a TFF-peptide because of the otherwise short contact time between the TFF-peptide and the surface of the eye. Another advantage of using mucoadhesive agents in the compositions of this invention is that they help to improve the protective layer on the ocular surface. Examples of mucoadhesives for use in the present invention include, but are not limited to, Carbopol®, pectin, alginic acid, alginate, chitosan, hyaluronic acid, polysorbates, such as polysorbate-20, -21, -40, -60, -61, -65, -80, -81, -85; poly(ethyleneglycol), such as PEG-7, -14, -16, -18, -55, -90, -100, -135, -180, -4, -240, -6, -8, -9, -10, -12, -20, or -32; oligosaccharides and polysaccharides, such as Tamarind seed polysaccharide, gellan, carrageenan, xanthan gum, gum Arabic, and dextran; cellulose esters and cellulose ethers; modified cellulose polymers, such as carboxymethylcellulose, hydroxyethylcellulose, hydroxypropyl methylcellulose, hydroxyethyl ethylcellulose; polyether polymers and oligomers, such as polyoxyethylene; condensation products of poly(ethyleneoxide) with various reactive hydrogen containing compounds having long hydrophobic chains (e.g. aliphatic chains of about 12 to 20 carbon atoms), for example, condensation products of poly(ethylene oxide) with fatty acids, fatty alcohols, fatty amides, polyhydric alcohols; polyether compounds, such as poly(methyl vinyl ether), polyoxypropylene of less than 10 repeating units; polyether compounds, such as block copolymers of ethylene oxide and propylene oxide; mixtures of block copolymers of ethylene oxide and propylene oxide with other excipients, for example poly(vinyl alcohol); polyacrylamide; hydrolyzed polyacrylamide; poly(vinyl pyrrolidone); poly(methacrylic acid); poly(acrylic acid) or crosslinked polyacrylic acid, such as Carbomer®, i.e., a homopolymer of acrylic acid crosslinked with either an allyl ether of pentaerythritol, an allyl ether of sucrose, or an allyl ether of propylene. Preferably, the mucoadhesive component is Tamarind seed polysaccharide, carboxymethylcellulose, hydroxymethylcellulose, Carbopol, hyaluronic acid, xanthan gum, or alginate. The most preferred mucoadhesive component is Tamarind seed polysaccharide, which is a galactoxyloglucan that's extracted from the seed kernel of *Tamarindus Indica*, and can be purchased from TCI America of Portland, Oreg.

In certain situations it is also advantageous to include a second therapeutically active agent in any of the compositions described herein related to this invention. The second therapeutically active agent could be any drug which might be useful in treating the symptoms of dry eye, or any of its underlying causes. In addition, the second therapeutically active agent could be any drug which is useful in preventing or treating any disease which might occur simultaneously to dry eye disease, whether or not the disease is related. In another useful aspect of this invention, the second therapeutically active agent could be a drug which is used in topical ophthalmic compositions which might cause, contribute to, or aggravate dry eye disease as a side effect of its use. In this aspect, this invention is useful in reducing or eliminating said side effect.

One class of useful second therapeutically active agents in relation to this invention is nucleotide purinergic receptor agonists such as uridine 5'-triphosphate, dinucleotides, cytidine 5'-diphosphate, adenosine 5'-diphosphate, $P^1$-(cytidine 5'-)-P-(uridine 5'-)tetraphosphates, $P^1$, $P^4$-di(uridine 5')-tetraphosphates, or their therapeutically effective analogues or derivatives, which may affect tear secretion, particularly the mucous layer of tears, and thus may have potential in treating dry eye disease. These compounds are described in the following patents, all of which are incorporated herein by reference: U.S. Pat. No. 6,555,675; U.S. Pat. No. 6,548,658; U.S. Pat. No. 6,436,910; U.S. Pat. No. 6,348,589; U.S. Pat. No. 6,331,529; U.S. Pat. No. 6,323,187; U.S. Pat. No. 6,319,908; and U.S. Pat. No. 5,900,407.

Another useful class of compounds that are useful as second therapeutically active agents is nicotinic receptor agonists such as nicotine and its analogs, trans-metanicotine and its analogs, epibatidine and its analogs, pyridol derivatives, piperidine alkaloids such as lobeline and its analogs, certain para-alkylthiophenol derivatives, and imidacloprid and its analogs. These compounds are believed to stimulate secretion of mucin by the conjunctival goblet cells, and thus may be useful in treating dry eye, as disclosed in U.S. Pat. No. 6,277,855, which is incorporated herein by reference.

Another useful class of second therapeutically active agents in relation to this invention is tetracycline, derivatives or analogues of tetracycline, or chemically modified tetracycline. These compounds are believed to have potential in correcting delayed tear clearance, as described in U.S. Pat. No. 6,455,583 B1, incorporated herein by reference, which is related to some cases of dry eye.

Another class of compounds that are useful as second therapeutically active agents is corticosteroids such as methylprednisolone sodium succinate, prednisolone acetate, prednisolone sodium phosphate, fluorometholone, fluorometholone acetate, dexamethasone sodium phosphate, hydroxymethylprogesterone, rimexolane, budesonide, and tixocortol pivalatein, which are believed to be useful in treating dry eye as disclosed in U.S. Pat. No. 6,153,607, incorporated herein by reference.

Another class of compounds which are useful as second therapeutically active agents is products of human lacrimal gland acinar epithelia such as growth factors or cytokines including the transforming growth factor beta (TGFβ), which are disclosed to be useful in treating dry eye in U.S. Pat. No. 5,652,209, incorporated herein by reference.

Another class useful second therapeutically active agents is androgens or androgen analogues such as 17α-methyl-17β-hydroxy-2-oxa-5α-androstan-3-one, testosterone or testosterone derivatives, 4,5α-dihydrotestosterone or derivatives, 17β-hydroxy-5α-androstane and derivatives, 19-nortestosterone or derivatives, and nitrogen-substituted androgens, which are taught to be useful in treating dry eye disease in the following patents which are incorporated herein by reference, U.S. Pat. No. 6,107,289; U.S. Pat. No. 5,958,912; U.S. Pat. No. 5,688,765; and U.S. Pat. No. 5,620,921.

Another useful class of second therapeutically active agents is cyclosporin and cyclosporin derivatives, such as cyclosporin A, cyclosporin B, cyclosporin C, cyclosporin D, and cyclosporin G.

In relationship to any of the compositions described herein, it is preferable that an effective amount of buffer be included to maintain the pH from about 6 to about 8, preferably about 7. Buffers used are those known to those skilled in the art, and, while not intending to be limiting, some examples are acetate, borate, carbonate, citrate, and phosphate buffers. Preferably, the buffer comprises borate. An effective amount of buffer necessary for the purposes of this invention can be readily determined by a person skilled in the art without undue experimentation. In cases where the buffer comprises borate, it is preferable that the concentration of the borate buffer be about 0.6%.

In any of the compositions related described herein related to this invention, it is preferable for a tonicity agent to be used. Tonicity agents are used in ophthalmic compositions to adjust the concentration of dissolved material to the desired isotonic range. Tonicity agents are known to those skilled in the ophthalmic art, and, while not intending to be limiting, some examples include glycerin, mannitol, sorbitol, sodium chloride, and other electrolytes. Preferably, the tonicity agent is sodium chloride.

In any of the compositions related to the present invention which are described herein, it is preferable for a preservative to be used when the composition is intended for multiple use. There may also be reasons to use a preservative in single use compositions depending on the individual circumstances. The term preservative has the meaning commonly understood in the ophthalmic art. Preservatives are used to prevent bacterial contamination in multiple-use ophthalmic preparations, and, while not intending to be limiting, examples include benzalkonium chloride, stabilized oxychloro complexes (otherwise known as Purite®), phenylmercuric acetate, chlorobutanol, benzyl alcohol, parabens, and thimerosal. Preferably, the preservative is benzalkonium chloride (BAK).

Under certain circumstances, a surfactant might be used in any of the compositions related to this invention which are described herein. The term surfactant used herein has the meaning commonly understood in the art. Surfactants are used to help solubilize the therapeutically active agent or other insoluble components of the composition, and may serve other purposes as well. Anionic, cationic, amphoteric, zwitterionic, and nonionic surfactants may all be used in this invention. For the purposes of this invention, it is preferable that a nonionic surfactant, such as polysorbates, poloxamers, alcohol ethoxylates, ethylene glycol-propylene glycol block copolymers, fatty acid amides, alkylphenol ethoxylates, or phospholipids, is used in situations where it is desirable to use a surfactant.

Another type of compound that might be used in any composition of this invention described herein is a chelating agent. The term chelating agent refers to a compound that is capable of complexing a metal, as understood by those of ordinary skill in the chemical art. Chelating agents are used in ophthalmic compositions to enhance preservative effectiveness. While not intending to be limiting, some useful chelating agents for the purposes of this invention are edetate salts, like edetate disodium, edetate calcium disodium, edetate sodium, edetate trisodium, and edetate dipotassium.

A particularly preferred embodiment of this invention comprises a trefoil factor family peptide, tamarind seed polysaccharide, about 0.5% sodium chloride, about 0.005% benzalkonium chloride, and about 0.6% of a borate buffer wherein the pH of the composition is adjusted to from about 6 to about 8.

Another aspect of this invention involves a method of preventing or treating dry eye in a person, comprising topically administering to the eye of said person any one of the compositions described herein as related to this invention, which composition comprises a therapeutically effective amount of a trefoil factor family peptide.

Another aspect of this invention involves a pharmaceutical product comprising any one of the compositions described herein as related to this invention, which composition comprises a therapeutically effective concentration of a trefoil factor family peptide, which is dispensed from a package suitable for ophthalmic use, and wherein the use of the composition for the prevention or treatment of dry eye is indicated thereon.

The best mode of making and using the present invention are described in the following examples. These examples are given only to provide direction and guidance in how to make and use the invention, and are not intended to limit the scope of the invention in any way.

EXAMPLE 1

Compositions related to this invention are prepared by the following procedure. Unless otherwise indicated, all procedural steps are carried out at room temperature.

Part I

TSP is added to purified water at the concentration indicated in the Table 1, and the solution is brought to a boil and maintained at a gentle boil for about 30 minutes. The solution is then allowed to cool to room temperature, and water is added to compensate for evaporative loss during boiling. The solution is then filtered through a 20 micron clarity filter followed by a 0.45 micron sterilizing filter.

Part II

Each component listed in Table 1 is added in amount needed to provide the indicated concentration to a fixed volume of the solution from part I, in the following order: TFF 1, boric acid, sodium borate decahydrate, sodium chloride, and BAK. After the addition of each component, the mixture is stirred until the solute is completely dissolved before the next component is added. When all of the components of the formulation have been added and dissolved, the pH is then adjusted to 7.0 with NaOH or HCl. The solution is then sterile filtered.

TABLE 1

| Component | Function | % (w/v) |
|---|---|---|
| TFF1 | TFF-peptide | 0.15 |
| Tamarind Seed Polysaccharide (TSP) | Mucoadhesive | 0.5 |
| Boric Acid | Buffer | 0.6 |
| Sodium Borate Decahydrate | Buffer | 0.035 |
| Sodium Chloride | Tonicity Agent | 0.53 |
| Benzalkonium Chloride (BAK) | Buffer | 0.005 |
| Purified Water | | Q.s. |
| HCl or NaOH | Buffer | adjust to pH 7.0 |

EXAMPLE 2

A formulation having the composition of Table 2 is prepared according to an analogous procedure to that of Example 1.

TABLE 2

| Component | Function | % (w/v) |
|---|---|---|
| TFF3 | TFF-peptide | 0.15 |
| Tamarind Seed Polysaccharide (TSP) | Mucoadhesive | 0.5 |
| Boric Acid | Buffer | 0.6 |
| Sodium Borate Decahydrate | Buffer | 0.035 |
| Sodium Chloride | Tonicity Agent | 0.53 |
| Benzalkonium Chloride (BAK) | Buffer | 0.005 |
| Purified Water | | Q.s. |
| HCl or NaOH | Buffer | adjust to pH 7.0 |

EXAMPLE 3

A formulation having the composition of Table 3 is prepared according to an analogous procedure to that of Example 1.

TABLE 3

| Component | Function | % (w/v) |
|---|---|---|
| TFF 1 | TFF-peptide | 0.15 |
| Sodium Carboxymethylcellulose | Mucoadhesive | 0.5 |
| Boric Acid | Buffer | 0.6 |
| Sodium Borate Decahydrate | Buffer | 0.035 |
| Sodium Chloride | Tonicity Agent | 0.53 |
| Benzalkonium Chloride (BAK) | Buffer | 0.005 |
| Purified Water | | Q.s. |
| HCl or NaOH | Buffer | adjust to pH 7.0 |

EXAMPLE 4

A formulation having the composition of Table 4 is prepared according to an analogous procedure to that of Example 1.

TABLE 4

| Component | Function | % (w/v) |
|---|---|---|
| TFF 3 | TFF-peptide | 0.15 |
| Hydroxypropylmethylcellulose | Mucoadhesive | 0.5 |
| Boric Acid | Buffer | 0.6 |
| Sodium Borate Decahydrate | Buffer | 0.035 |
| Sodium Chloride | Tonicity Agent | 0.53 |
| Benzalkonium Chloride (BAK) | Buffer | 0.005 |
| Purified Water | | Q.s. |
| HCl or NaOH | Buffer | adjust to pH 7.0 |

EXAMPLE 5

A formulation having the composition according to Table 5 is prepared according to the method described in U.S. Pat. No. 5,981,607, incorporated herein by reference, with the cyclosporin A being added to the castor oil before introducing the oil into the emulsion. An aqueous solution of the trefoil factor family peptide is sterile filtered into the emulsion after the emulsion has cooled.

TABLE 5

| Component | Function | % (w/v) |
|---|---|---|
| TFF 3 | TFF-peptide | 0.15 |
| Cyclosporin A | Second Therapeutically Active Agent | 0.05 |
| Castor oil | Oil phase | 1.25 |
| Polysorbate-80 | Surfactant | 1.0 |
| Pemulen TR-2 | Emulsion stabilizer | 0.05 |
| Glycerin | Tonicity agent | 2.2 |
| Purified Water | | Q.s. |
| HCl or NaOH | Buffer | adjust to pH 7.4 |

EXAMPLE 6

A drop of a composition prepared according to one of Examples 1–5 is added at least once a day to a patient suffering from dry eye disease. Relief of symptoms is experienced and continues for as long as the patient is receiving the treatment.

What is claimed is:

1. A composition comprising a therapeutically effective amount of trefoil factor family peptide, an effective amount of tamarind seed polysaccharide, about 0.5% sodium chloride, about 0.005% benzalkonium chloride, and about 0.6% of a borate buffer, and wherein said composition has a pH of from about 6 to 8.

2. A method of preventing or treating dry eye in a person comprising topically administering to the eye of said person a composition comprising a therapeutically effective amount of trefoil factor family peptide, an effective amount of tamarind seed polysaccharide, about 0.5% sodium chloride, about 0.005% benzalkonium chloride, and about 0.6% of a borate buffer, and wherein said composition has a pH of from about 6 to 8.

3. A pharmaceutical product comprising a composition comprising a therapeutically effective amount of trefoil factor family peptide, an effective amount of tamarind seed polysaccharide, about 0.5% sodium chloride, about 0.005% benzalkonium chloride, and about 0.6% of a borate buffer, and wherein said composition has a pH of from about 6 to 8.

* * * * *